United States Patent
Mongan et al.

(10) Patent No.: US 9,717,325 B2
(45) Date of Patent: Aug. 1, 2017

(54) RECHARGEABLE FACIAL BRUSH WITH STERILIZATION

(71) Applicants: Ryan Mongan, Orange, CA (US);
Simon Ghahary, Long Beach, CA (US)

(72) Inventors: Ryan Mongan, Orange, CA (US);
Simon Ghahary, Long Beach, CA (US)

(73) Assignee: TAO CLEAN, LLC, Orange, CA (US)

( * ) Notice: Subject to any disclaimer, the term of this patent is extended or adjusted under 35 U.S.C. 154(b) by 0 days.

(21) Appl. No.: 14/702,864

(22) Filed: May 4, 2015

(65) Prior Publication Data
US 2015/0313354 A1    Nov. 5, 2015

Related U.S. Application Data

(60) Provisional application No. 61/987,930, filed on May 2, 2014.

(51) Int. Cl.
| | |
|---|---|
| *A46B 17/06* | (2006.01) |
| *A47K 7/02* | (2006.01) |
| *A47K 7/03* | (2006.01) |
| *A61L 2/10* | (2006.01) |
| *A61L 2/24* | (2006.01) |

(52) U.S. Cl.
CPC ............ *A46B 17/06* (2013.01); *A46B 17/065* (2013.01); *A47K 7/02* (2013.01); *A47K 7/03* (2013.01); *A61L 2/10* (2013.01); *A61L 2/24* (2013.01); *A46B 2200/1006* (2013.01); *A61L 2202/14* (2013.01)

(58) Field of Classification Search
CPC ........ A46B 17/06; A46B 17/065; A47K 7/02; A47K 7/03; A61L 2/00; A61L 2/10; A61L 2/24
See application file for complete search history.

(56) References Cited

U.S. PATENT DOCUMENTS

| | | | | |
|---|---|---|---|---|
| 5,127,521 A | * | 7/1992 | Bourque | A61L 2/10 206/15.2 |
| 6,494,315 B2 | * | 12/2002 | Frisk | B44D 3/123 206/15.3 |
| 6,994,212 B2 | * | 2/2006 | Bar Noy | A47K 1/09 206/209.1 |

(Continued)

FOREIGN PATENT DOCUMENTS

CN    202761662 U  *  3/2013

*Primary Examiner* — Shay Karls
(74) *Attorney, Agent, or Firm* — Maxvalueip LLC

(57) ABSTRACT

In one example, we describe a method and system for facial brush or body brush, for cleaning the skin. In one example, it utilizes distinct parts: a powered facial brush handle with the ability of offering both an oscillating and rotary setting, removable brush heads of varying materials and compositions, and a charging base station with a protective germicidal UVC sanitizing and drying chamber. User convenience is also central to our solution. All the functional actions of the protective germicidal UVC sanitizing and heating chamber are activated once the brush handle and brush head is placed within it, in one example. Mode control allows the user to choose the right setting for them, offering a mild setting for sensitive skin and normal for balanced skin types. A set duration of brush activation allows the user to orchestrate a complete cleaning. Various examples and variations are presented.

18 Claims, 12 Drawing Sheets

(56) References Cited

U.S. PATENT DOCUMENTS

2003/0034459 A1* 2/2003 Bonin .................. A61L 2/06
250/491.1
2010/0281636 A1* 11/2010 Ortins et al. ............ A46B 9/04
15/4

* cited by examiner

RECHARGEABLE FACIAL BRUSH WITH STERILIZATION

RELATED APPLICATIONS

This application is related and gets the benefit of the priority date and filing date of the prior (provisional) US patent application filed May 2, 2014, Ser. No. 61/987,930, with the same assignee. All of the teachings of the provisional case are incorporated herein, by reference, as well as the teachings of another of our application titled "Toothbrush Sterilization System", Ser. No. 14/604,729, filed 25 Jan. 2015, which are also incorporated herein, by reference.

BACKGROUND OF THE INVENTION

Personal cleaning is first recorded on ancient tablets from Sumeria as part of religious ritual. While evidence of soaps have been found in Babylon and Egypt from approximately 2,800 BCE, it is conjectured that these were most likely used for cleaning materials such as fabrics. It was quite a time after that soaps were effective and in widespread use for cleaning the human body. In this interim time, a device known as a strigil was developed presumably by the Greeks. Few writings exist from the time, but strigil artifacts have been found from sites dating from the 6th century BCE.

The strigil was a curved blade of metal that was used to scrape against the skin. A mixture of olive oil and sand (or sometimes pumice or ash) was rubbed into the skin and the strigil was then used to scrape the skin clean. This was an effective exfoliant as it not only removed sweat and dirt but also removed dead skin and opened up pores. It is unknown if they were used by the masses, as writings and sculptures were not focused on the mass public. Strigil use was commonly associated with athletes, such as wrestlers. One of the most renown early images of the strigil in use is the sculpture Apoxyomenos by Lysippus in the Vatican created in ~330 BCE.

The Romans adopted and continued the use of the strigil as an integral routine of the Roman baths. Accounts of the strigil in the baths date to the 1st century BCE, where it was commonly used to condition the skin prior to entering the waters. Galen (130ACE-~200), a prolific Greek physician/philosopher, wrote extensively about the strigil and its beneficial uses, as a skin conditioning and cleansing device.

In George Cheyne's 1754 writing, "An Essay of Health and Long Life", a new term is noted, that of a Flesh Brush. While it contained the word brush, it probably did not contain bristles similar to today's brushes. It was more likely resembled an ancient strigil, since in his writings, it is synonymous with an animal curry comb. These writings still portray the device as beneficial to human health. At this point, bristled brushes were still a rarity. The first hair brush manufacturer is believed to be Kent Brushes, which was formed in 1777. These were at the time very expensive items, and it took as many as 12 workers to complete one brush.

In MacMicking's 1851 work "Recollections of Manilla and the Philippines", the author mentions bathing with soap and a flesh-brush. In this case, bristles are mentioned. It is assumed by this point that the term flesh brush has morphed or is in the presence of morphing from that of a bladed instrument to one with bristles. By the 1880s and 1890s, patents were appearing in the US Patent Office for flesh brushes. These depicted brushes with bristles and were widely referenced in the art.

Today, the term flesh brush has fallen into disuse. Brushes that accomplish the same purpose, that of deep skin cleaning and exfoliation, are termed body brushes and facial brushes. Early powered brushes for skin treatment are taught by Friedmann U.S. Pat. No. 3,272,200 and Shjoi U.S. Pat. No. 3,906,940. With the advent of batteries as a popular power source, these powered brushes surface again to become hand-held items. Abura U.S. Pat. No. 4,203,431 demonstrates this. These brushes taught rotational motion, but other motions such as oscillating (Pilcher U.S. Pat. No. 7,320,691) and combination movements (Gutelius U.S. Pat. No. 6,253,405) are also taught in the prior art.

As opposed to hair brushes and barber dust off brushes, which are generally used dry, these body and facial brushes are intended to be used with cleansers and in a wet state. Many are completely waterproof and are used while bathing. Because of their closely residing tufts of bristles, the brush heads can retain water, as well as skin particles, bodily fluids, and pathogens. This was not a problem with the strigil. It contained no bristles and dried quickly. Since current body and facial brushes remain wet for a significant amount of time after usage, they can be a breeding ground for a broad range of fungal, bacterial, parasitic, and viral agents. While the epidermis is generally a very good defender against such maladies, the very purpose of these brushes is to abrade the skin. This can subject the user to a variety of maladies including: dermatitis, urticaria, angioedema, cold sores, necrotizing fasciitis, cellulites, infectious myositis, etc.

The brush head can also act as a fomite and repeatedly carry pathogens, such as germs, to expose the solitary user or, if the device is shared, from one individual to another. None of the current powered facial brushes offer cover or sterilize the brush head in order to make sure that it is kept clean and ready in between use. This leaves it exposed to the environment. As this is left to the discretion of the user, it can be especially problematic due to the popular location of the device, namely, the bathroom. This environment typically has many sources of water flow (e.g. sinks, showers, toilets and bathtubs). These water sources aerosolize water droplets. The water droplets can transport other elements such as urine, feces, and saliva throughout the bathroom. They can also be exposed to airborne chemical pollutants from aerosols, such deodorants or air fresheners commonly used within the contained environment of the bathroom. Since the bristles are exposed to this environment, they can become inadvertently contaminated. If the brush head is not stored and cleaned correctly, it not only negates the benefits of its use, it can cause new problems like infections by carrying bacteria to the skin. This could aggravate the preconditions it was originally designed to solve.

SUMMARY OF THE INVENTION

During the past decade, motorized facial brushes have grown in popularity for personal care. In combination with facial cleansers and soaps a motorized brush head removes more sebum and blackheads than traditional hand cleaning to clean pores more efficiently, enhancing the personal cleanliness routines of the user.

Consistent to market trends, the brush includes a housing, a handle, which can be held in one hand, and a brush head. The handle contains a motor to drive the brush head and an electrical circuit for controlling power, an ON/OFF switch and in some cases, speed or power modes to regulate the strength of the motor, and a control switch. The brushes are either corded to an external power source or contain an internal power source. The internal power source could either be disposable batteries or a rechargeable power source such as rechargeable batteries or a capacitor. The rechargeable version also consists of a charging base that, in some cases, doubles up as the brush stand. The brush head, itself, is either a conventional brush type, typically consisting of a circular brush head, housing a plurality of nylon bristles extending outward from the bristle face of varying thickness, or a closed foam structure type, soft and smooth on the working surface. Traditionally, a brush that oscillates drives the foam-based head. In most cases, bristles or foam heads types are removable and replaceable, and operatively connected either on axis on the same plane to the brush motor or tilted at an inclination angle.

These motorized brushes can currently be categorized in one of two versions available. The first are for brushes that contain an oscillating motor. This works on a high frequency to resonate the brush head backwards and forwards at a very high speed causing the head to vibrate. The second is of rotary action, which when activated spins the brush head continuously in one direction. Both have their advantages, mainly translated into user experience preferences. The rotary is perceived as more powerful, but the oscillation is more popular with people who have sensitive skin.

A typical user will first moisten the face and neck area with water, and then apply cleanser directly to the moistened skin or to a damp brush head. They will then first, if available, select the desired speed or power mode, and then push the ON/OFF button to turn on the facial brush. The user will then move the brush head around the moistened face and neck area. After use, the brush will turn off automatically or the user will push the ON/OFF button and rinse the brush head and place and store on a passive or rechargeable stand, counter top or shower rack, usually within the bathroom area or in close proximity to where the cleaning process was started.

The brush acts as a barrier between the user's hands and the facial area they are cleaning. This helps to negate the possibility of transporting bacteria or dirt from the hands to the facial area. This is particularly useful for those avoiding blocked pores or aggravating chronic skin conditions such as acne. However, brush storage can be problematic. None of the current facial brushes on offer cover or sterilize the brush head, in order to make sure that it is kept clean and ready in between use. This leaves it exposed to the environment. As this is left to the discretion of the user, it can be especially problematic due to the popular location of the device, i.e., the bathroom. This environment typically has many sources of water flow (e.g. sinks, showers, toilets and bathtubs). These water sources aerosolize water droplets. These water droplets can transport other elements such as urine, feces, and saliva throughout the bathroom. They can also be exposed to airborne chemical pollutants from aerosols, such as deodorants or air fresheners commonly used within the contained environment of the bathroom. Since the bristles are exposed to this environment, they can become inadvertently contaminated. If the brush head is not stored and cleaned correctly, it not only negates the benefits of its use, but it can also cause new problems like infections by carrying bacteria to the skin. This could aggravate the preconditions it was originally designed to solve.

Furthermore, many facial brush manufacturers fail to enforce or choose to ignore over-use of the facial brushes. Over-use or obsessive use can aggravate or damage the sensitive facial area of the skin, leading it to be stripped of precious oils and open to bacteria, infection, and inflammation. This can defeat the positive attributes of the facial brush itself, turning it to be a destructive tool exposing the user to sensitivity from products that follow the post exfoliation skin regime, such as moisturizers, make-up or sun care lotions. Stripping the skin of these nutrients in some users can make the skin surface more prone to the sun damage that in turn can make the user more susceptible to UV damage or sunburn, which can lead to Melanoma. In some cases, where a previous skin condition exists, it can not only aggravate the condition, but also dramatically perpetuate the problem.

Most facial brush manufacturers adopt a one size fits all attitude when offering cleaning surfaces for the user's skin. However, this is not the case for skin types or ethnicity, which can range from hard to normal to sensitive to supersensitive. This is especially true when answering the needs of users with pre-existing skin conditions, which require extra-care when cleansing or having inflamed or irritated skin.

This led us to create an invention that is built around the solution to answer the above problems. Our invention utilizes two distinct parts: a powered facial brush handle with the ability of offering both an oscillating and rotary setting, removable brush heads of varying materials and compositions, and a charging base station with a protective germicidal UVC sanitizing and drying chamber.

User convenience is also central to our solution. All the functional actions of the protective germicidal UVC sanitizing and heating chamber are activated once the brush handle and brush head is placed within it.

Although we are primarily concerned with keeping the facial brush head clean, sanitized, and charged, the user experience encourages good practice when operating the Brush Device. For daily use, Mode control allows the user to choose the right setting for them, offering a mild setting for sensitive skin and normal for balanced skin types. The oscillating motion of the Brush Device delivers these daily modes, whilst the rotary action activates the more powerful settings for deep exfoliation, which we advise to be used infrequently.

A set duration of brush activation allows the user to orchestrate a complete clean of the facial area within an optimum cleaning time. The optimum cleaning time is a set duration divided into timed segments that relate to a working pattern for the user. Each segment to an area on the face and neck and a simple pause prompts the user to move from one area to another ensuring a complete clean of the face and neck area. This procedure is a timed pattern of brush motor operation corresponding to quadrants on the body, e.g., face and neck, with each pause encouraging the user to move from one area to another area, or sounding a beep or flashing light, to warn or inform the user to end one section and go to another, as the timer prevents over-doing or under-doing one section of the skin, for optimum results.

A part of the solution was to develop a range of brush heads that would complement the settings and address particular skin types or conditions. We looked at the culture of cleanliness to be mindful of the long-term efficiency of an enhanced exfoliation routine and designed specific brush head types to use in conjunction with our findings.

Practical Considerations:

In an embodiment, the protective germicidal UVC sanitizing and drying chamber (Base Station) allows the user to protect, clean, and charge their facial brush handle and brush head (Brush Device).

Our current invention incorporates an integrated charging station, sterilization and drying chamber. This Base Station is either corded to AC power or runs on its own internal battery or capacitor. The Base Station (40) includes a recessed entrance (58) to the internal germicidal UV sanitizing chamber, which is located central on top of the device. The external material of the charging base would be glass, BPA free plastic, or a resin based material. The recessed Base Station entrance (58) (female) corresponds to the bottom of the Brush Device (16) and brush head design (male).

In an embodiment, optionally, the material for the internal wall of the Base Station would be quartz glass or a UVC transparent thermoplastic, allowing undisturbed distribution of the germicidal UVC rays. As the UVC light source (46) is behind a transparent barrier, we minimize the possibly of the user touching it directly. Another option is for an exposed germicidal UVC bulb or other germicidal UVC light source. The Base Station can easily be accessed for cleaning, maintenance, or replacing, and could be completely waterproof.

Once it is inserted in the Base Station, the brush head (12) is removed from the environment, which keeps it cleaner and more sterile than being left outside between uses. This helps to solve the issue raised in the current art mentioned above. The Brush Device (10) has an internal charging coil (14) near the brush head end. This creates a non-contact inductive coupling between this coil and a similar coil in the Base Station (54). Optionally, direct electrical connection contacts between the Brush Device and Base Station could make this charge coupling. Once the base detects the presence of the facial brush, the charging commences and the sterilization and the optional heating cycle begin. A heater within the Base Station (52) could create the drying cycle. This would utilize the design of the inner chamber to act like a chimney to transfer flue gases to the external environment, via stack effect (FIG. 9a).

The circulated air aids and speeds the drying process of the Brush Head. Room temperature air is brought in using a small clearance underneath the Base Station Chamber. It exhausts via the small gap between the Base Station and the Brush Device. The inclusion of an internal motorized fan within the Base Station could help increase the exchange of airflow and reduce the drying time of the Brush Head. The gap mentioned above between the brush handle and recessed neck of the chamber is achieved through fins (42) strategically placed on the inside of the inner chamber entrance wall. This allows for Brush Device to be supported on the fins creating a gap with even distance between the handle and inner Base Station wall.

Also, once placed within the recess the Base Station, the Brush Device is held stable. The two distinct shapes of the design fit together. The tapered cylindrical handle and the fluted aperture of the chamber allow the brush occluding the vast majority of the opening and the facial brush head to be covered. It also reduces any escaped pollution caused by stray UVC Rays activated from the sterilizing light frequencies of the UVC source within. Also, once the brush device is inserted into the Base Station, the current design is such that the brush head is prevented from touching the light source.

This slip fit between the two parts creates two advantages. One, it allows the user to remove the brush handle with one hand. The base does not have to be held down, fixed or otherwise excessively weighted, and two, a path for water vapor to escape the chamber base. This is advantageous in that it aids in drying the facial brush head and any water on the contact ring would dry. Without a gap, the water becomes trapped between the two parts.

The sterilization is accomplished by means of a UVC light source within the Base Station (40). This UVC light source wraps around the brush head immersing it, eliminating shadows directed at the entire surface of the brush head and any retained pathogens (e.g. virus, bacteria, prion, parasite, or fungus) captured therein. This ring light could be a mercury vapor tube light. It could also be a series of point light sources that wrap around the brush head, like for instance UVC LEDs or laser sources. This light has a spectral wavelength centered roughly around 240 nm, as an example. The wavelength range of UVC light is 100-280 nm, as an example. While the light sources may emit light outside of this range, into the visible spectrum for example, it is the light within this range that has germicidal benefits. Optionally, an additional UVC source could be placed within the Brush Device above the base of the brush head housing to maximize the exposed surfaces, thereby having fewer surfaces within shadows, consequently maximizing the surfaces that are exposed to the sterilizing, germicidal ultraviolet rays.

To further aide in the elimination of shadows, the interior of the Base Station sterilization chamber could be made reflective aiding the beams in uniform distribution to the Brush Head. A UVC light source reflector (62) could be comprised of a concave body with an inner reflective surface. This reflective surface redirects the light emitted from the UVC source back onto the brush head. This increases the intensity of light onto the brush head, thereby improving efficiency. It also enables light to be directed onto the brush head into areas that would be inaccessible without the reflection. Optionally, to further maximize the reflection coverage of the germicidal light source, the brush head itself could have a reflective panel behind the bristles. This would allow light to reflect back through the underside of the brush head and down the shafts of bristle themselves. Furthermore, a by-product of a germicidal UVC lamp, ozone, aids effectively to deodorize, disinfect, and destroy bacteria, fungi, allergens, and other odor-causing agents by oxidizing bacteria within the Base Station.

Optionally the material of the reflector could contain aluminum or metal or shiny surfaces or coatings or metal evaporations or sputtering or metal plating, that have been shown to optimize the reflection of UVC light very effectively.

A timer, electrically coupled between a power source and the germicidal light source, is triggered ON by the sensor system or proximity switch and supplies power to the lamp for a predetermined period of time, and thereafter, disconnects the power from the lamp, when the timer counts down and turns OFF. The amount of time could vary, based on the number of brush cycles that the facial brush has been through since the last cleaning. Optionally, the brush handle can keep track of usage and this information can be communicated to the Base Station, via means such as RFID tracking or Bluetooth communication or antenna or wired means. Since there can be a communication link between the brush and the Base Station, either of those could have a display to communicate information to the user. This display can show things like charging time remaining, sterilization time remaining, number of brushing cycles completed, life of brush head remaining, and average brushing duration.

The chamber of the design is devoid of crevices that could become water traps. If water drips off the brush head, the water falls through the device through an opening in the bottom of the chamber. Also, as the chamber is open on both ends and is lacking in crevices, it is very easy to clean. This addresses any problems with pathogens (e.g. virus, bacteria, prion, parasite, or fungus) cultivating molds or bacteria associated with bad sanitization. This water could reside on the countertop until it evaporates away. Alternatively, there could be a hydrophilic pad that resides below the chamber. This pad could wick the water throughout its volume or along its surface. Because the water is spread out, it has more evaporative surface area and is lost to the environment at a significantly accelerated rate. Optionally, this pad could have further functions such as a reflective surface that could further optimize the UVC light reflecting and directing up towards the brush head. Furthermore, as another option, the pad or Base Station design could include an additional UVC light source placed under the brush head.

Once the brush is inserted in the base, all activities are automatically activated. Since this takes no additional effort to accomplish from the user, it delivers on convenience.

In one embodiment, the Brush Device includes a housing of ergonomic design with a handle, can be held in one hand, which also includes a mechanism for holding a removable brush head. This allows the user to select the brush head of their choice. The external material of the Brush Device would be glass, BPA free plastic, or a resin based material. The handle also contains a motor to drive the brush head and a power supply, through a rechargeable battery or batteries, an electrical circuit for controlling power, and an ON/OFF switch. The present Brush Device design is waterproof.

The present Brush Device has an internal charging coil near the brush head end. This creates a non-contact inductive coupling between this coil and a similar coil in the Base Station. It would also contain a power mode button for the user to regulate the strength of the motor. This mode button may translate to settings that correspond to varying skin types, speeds, sensations or routines, making it easy for the user to recognize the setting they want. In one embodiment, the motor has the ability to shift from oscillating to rotary action. This action could be made via a gearing system or a controlled circuit regulating power movement that allows the motor to shift from oscillating back and forth into full rotation. Optionally, the brush device could contain two motors, one dedicated to each action oscillating or rotary, with a selection mechanism to switch between. The user, when selecting settings on the mode button, would interpret this shift as seamless.

In consideration of the frequency of Brush Device use and to answer the needs of our user's skin types, we have developed a range of optional removable Brush Heads. These designs complement the motor action, mode selection and frequency of use. One such brush shape complements the contours and folds of the facial area. The angular nature of the brush has been designed to reach into these regions of the face, such as the nose and top lip area to efficiently deliver a more detailed exfoliation that is hard to achieve by using the traditional circular brush head alone.

The user experience encourages good practice when operating the Brush Device through simple-to-follow prompts built into the operation activation. The first is a timed operational use of the brush motor that allows the user to orchestrate a complete clean of the facial area within an optimum cleaning time. The optimum cleaning time is, e.g., 1 minute, and, e.g., we have divided this into four timed segments of 15 seconds. To relate this to a working pattern for the user, we have divided the face into, e.g., four quadrants, and in this order: forehead, cheeks, nose and chin area, and lastly the neck. A simple pause to indicate each successive timed segment prompts the user to move from one area to the other area, ensuring a complete clean of the face and neck area. Leading the user in this way also helps the user move away from excessive cleaning of one area, particularly when using brush head types that exfoliate deeper.

DETAILED DESCRIPTION OF THE PREFERRED EMBODIMENTS

To solve these shortcomings of present day motorized facial and body brushes, the present invention consists of a system of a brush and a sterilizer. Between uses, the user docks the brush with the sterilizer. The operating end of the brush (that containing the bristles) resides within the sterilizer and is treated. The handle of the brush remains outside the sterilizer so the user can easily retrieve the device and utilize it. By removing the brush head from the environment, it is kept cleaner than being left outside between uses. This helps to solve the issue raised in the current art mentioned above. In one embodiment, the sterilizer consists of an ultraviolet lamp. While also producing some emissions in the visible spectrum, the functional range of the lamp (which produces the sterilization effect) is centered around a wavelength of approximately 240 nm. In addition to the direct germicidal effects of the ultraviolet (UV) light, ultraviolet lamps also produce ozone. This aids to deodorize, disinfect, and destroy bacteria, fungi, allergens, and other odor-causing agents by oxidizing bacteria in its presence.

While there are other strategies for sterilization (gas or liquid immersion, autoclave, vacuum, or rapid drying), UV sterilization is simple and cost effective. It has fewer parts, quiet, and is easily containable and maintainable. One disadvantage that UV sterilization has over some of the other solutions is that it utilizes light and light casts shadows. If a portion of the brush head intended for sterilization is in a shadow, the efficacy of the sterilization will be greatly reduced. Some prior art generic UV sterilizers (e.g., Milligan US 20120074334 A1) mention multiple UV lamps as a solution to get greater coverage. This, of course, directly increases manufacturing cost and would require a significant number of bulbs in order to achieve the complete coverage. Other prior art (e.g. Nevin U.S. Pat. No. 4,698,206) address this shortcoming by introducing reflective surfaces on the inside of the chamber. This also increases manufacturing costs and complete and uniform coverage is not a guarantee.

Figure 8:
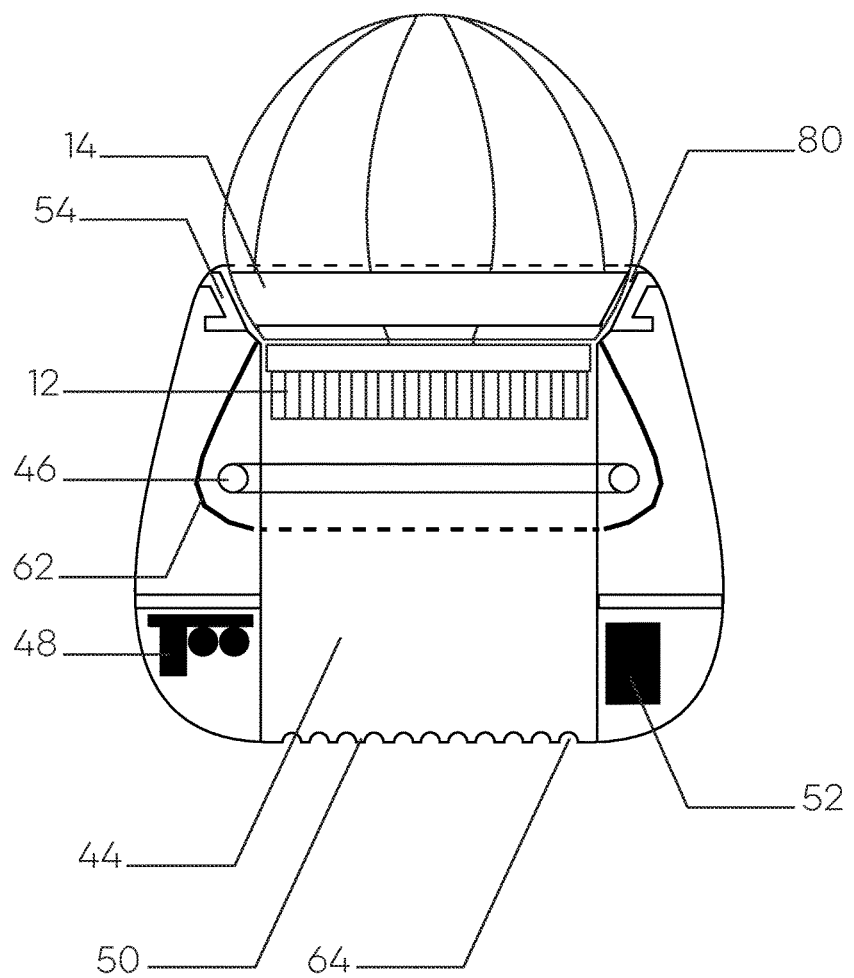
FIG. 8 is for one embodiment of our system diagram, as an example, for a single lamp in a ring configuration.

A typical method to create surfaces such as this is to sputter metal onto molded plastic surfaces. While effective, composite parts like this are difficult to recycle. In the present invention, we show a single lamp but that lamp is in a ring configuration (otherwise known as annular, torus, or donut), which is unique from the prior art (FIG. 8). The brush is placed within the ring so that light approaches the brush from a greater number of angles, greatly reducing or eliminating shadows. In practice, because of the end conditions of the lamp, the ring is interrupted. However this interruption is minor and most of the lamp retains the toroidal shape and the advantages thereof. In an alternative embodiment, the light source could be a series of point light sources that wrap around the brush head, like for instance UV-C LEDs.

In an embodiment, to further aide in the elimination of shadows, the interior of the Base Station sterilization chamber could be made reflective, aiding the beams in uniform distribution to the brush head. In an embodiment, a UV-C light source reflector could be comprised of a concave body with an inner reflective surface. This reflective surface redirects the light emitted from the UV-C source back onto the brush head. This increases the intensity of light onto the brush head, thereby improving efficiency. It also enables light to be directed onto the brush head into areas that would be inaccessible without the reflection. In an embodiment, optionally, to further maximize the reflection coverage of the germicidal light source, the brush head itself could have a reflective panel behind the bristles. This would allow light to reflect back through the underside of the brush head and down the shafts of bristle themselves.

As an option, in one embodiment, the Brush Device motor operation cycle could be activated by a sense of force exerted against the brush head. Once the force exceeds a certain threshold, the motor activates, using a sensor, small switch, mechanical devices, MEMS, or piezoelectric material. Optionally, once the force decreases below a threshold, the motor ceases.

One more option could utilize the entire surface or selected segments of the Brush Device as a means of operating the motor operation cycle. The user, through applying a sense of force exerted against the Brush Device handle, could start the motor operation cycle. This action could be repeated as a means to stop the motor operation cycle, as an example.

Optionally, this same concept could act as a means to control the power mode of the Brush Device motor. Through applying a sense of force exerted against the Brush Device handle surface or selected segments, the output power speed of the motor could accelerate, decrease or change modes. This concept can be used to ensure correct use of the Brush Device and disable it, if it was being used detrimentally. Too high a force could be damaging to skin. If the force exceeded pre-determined threshold, the motor could turn off or a signal could be sent to the user encouraging them to reduce force.

Optionally, as an example, the Brush Device could be one speed, with just ON/OFF button, and have replaceable batteries or a separate power supply outside of the Base Station.

In an embodiment, a timer, electrically coupled between a power source and the germicidal light source in the Base Station, is triggered ON by a sensor system or proximity switch, and supplies power to the lamp for a predetermined period of time, and thereafter disconnects the power from the lamp, when the timer counts down and turns OFF. The amount of time could vary, based on the number of brush cycles that the Brush Device has been through since the last cleaning. In an embodiment, optionally, the brush handle can keep track of usage, and this information can be communicated to the Base Station, via means such as RFID tracking or Bluetooth communication. Since there can be a communication link between the brush and the Base Station, either of those (or both) could have a display to communicate information to the user. This display can show things like charging time remaining, sterilization time remaining, number of brushing cycles completed, life of brush head remaining, or average brushing duration, among others.

In an embodiment, the sterilizer never contacts the brush and is not present directly underneath the brush face. If any drops of fluid were to fall off the brush head (12), they would fall completely through the Base Station (10) and reside on the counter on which it rests. While this does not eliminate the particulate, it ensures the fluid does not reside in a chamber, which may be inaccessible or hard to clean. All particulate can be removed from the countertop during regular counter cleaning routines. In an embodiment, alternatively, there could be a hydrophilic pad that resides below the chamber. This pad could wick the water throughout its volume or along its surface. Because the water is spread out, it has more evaporative surface area and is lost to the environment at a significantly accelerated rate. In an embodiment, optionally, this pad could have further functions, such as a reflective surface that could further optimize the UVC light reflecting and directing up towards the brush head. Furthermore, as another option, the pad or Base Station design could include an additional UVC light source placed under the brush head.

While the Brush Device is docked with the Base Station, the Brush Device is also charged. An embodiment shows an inductive coil at the upper end of the Base Station. When a mating coil in the Brush Device is brought in proximity with the Base Station's coil, energy can be transmitted from the Base Station to the Brush Device. This energy could charge batteries or energize a capacitor, either of which can act as the brush handle power source. Optionally, direct electrical connection contacts between the Brush Device and Base station could make this charge coupling.

In an embodiment, a brush dryer could be included in the sterilizer base. While the brush head is wet, it can act as a culture medium that can support the growth of microorganisms. If dried rapidly, this culture medium is disrupted and growth is stopped. The dryer could consist of a heater in the Base Station (52). This heater increases the temperature of the air around the brush (FIG. 9a). This increased air temperature volatizes water faster, and it also instigates airflow. The warmed air rises and passes out of the Base Station through a small gap (80) between the Base Station and the Brush Device. This gap is maintained via small ribs in the Base Station that touch off against the docked Brush Device. This small gap also allows fluid in this area to dry rather than becoming trapped. Make-up air (air that replaces the escaping warm air) is brought into the Base Station from the bottom. A small gap (64) exists between the sterilization base and the surface on which it sits. This air is then heated, and the process repeats itself.

In an embodiment, the inclusion of an internal motorized fan within the sterilization base could help increase the exchange of airflow and reduce the drying time of the brush head. This fan could operate on a continuous basis or on a duty cycle, or triggered by a controller connected to a humidity sensor, which turns on the fan, when high humidity (wet surface) is sensed. For a motorized brush, the brush head itself could act as the air mover and circulate the air. The brush handle, knowing via a sensor that it is docked (e.g., as a switch, to complete a circuit, to sense the docked position), could spin the brush head on a periodic basis to stir the air in the chamber and further decrease the drying time.

In an embodiment, good practice when operating the brush is encouraged, through simple-to-follow prompts built into its operation. The first is a timed operational use of the brush motor that allows the user to orchestrate a complete clean of the facial area within an optimum cleaning time. The cleaning time could be 1 minute, divided this into four timed segments of 15 seconds, as an example, or N segments of T seconds, where NT=1 minute. To relate this to a working pattern for the user, we have divided the face into four quadrants: forehead, cheeks, nose and chin area, and lastly the neck. A simple pause or light flashing or beeping sound, to indicate each successive timed segment, prompts the user to move from one area to the other, ensuring a complete clean of the face and neck area. Leading the user in this way also helps the user move away from excessive cleaning of one area, particularly when using brush head types that exfoliate deeper. In an embodiment, other body areas are cleaned with the same device.

Figure 1A:
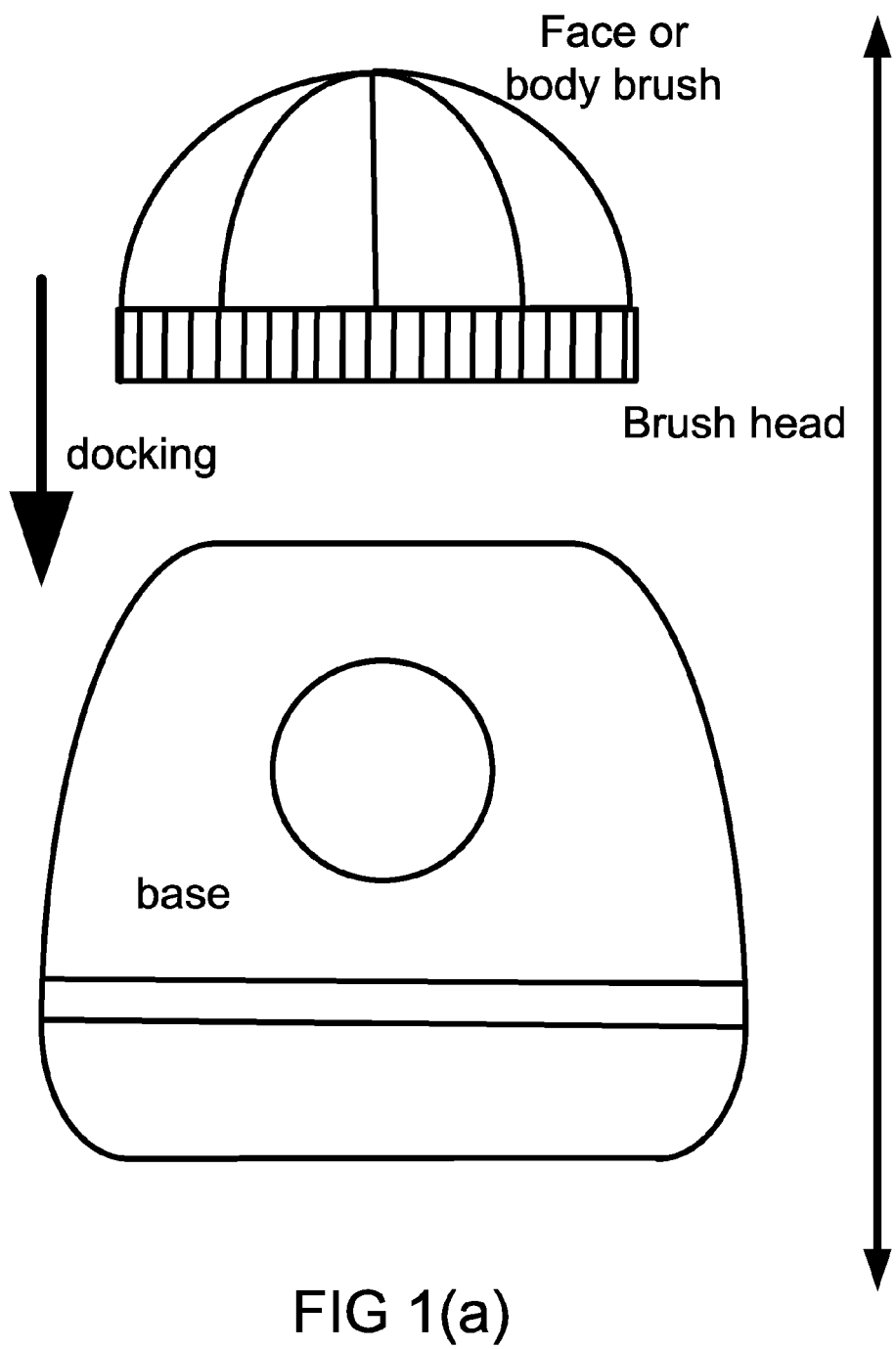
FIG. 1(a) is for one embodiment of our system, as an example, for a view of the base station with the brush device docking on it.
Figure 1B:
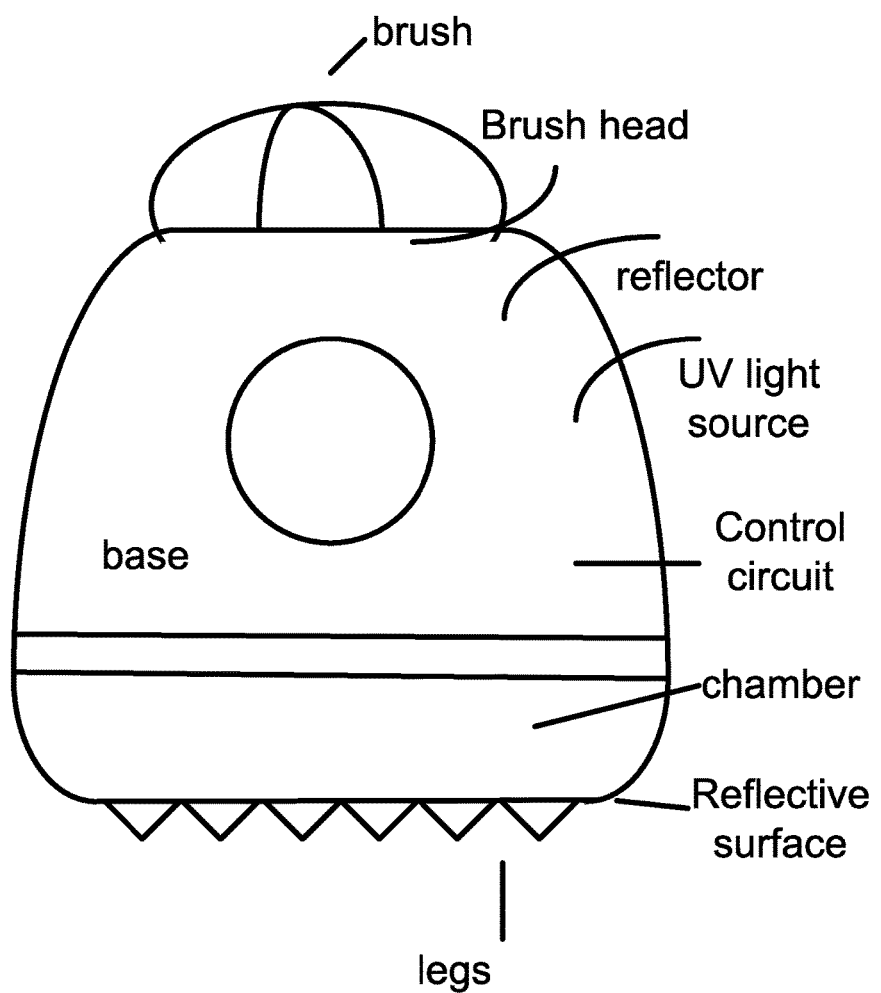
FIG. 1(b) is for one embodiment of our system, as an example, for a view of the base station plus brush device, with some of the internal components.

In an embodiment, we have the following systems and features: FIG. 1(*a*) is for one embodiment of our system, as an example, for a view of the base station with the brush device docking on it. FIG. 1(*b*) shows one embodiment of our system, as an example, for a view of the Base Station plus Brush Device, with components brush, brush head, reflector, UV light, control circuit, chamber, reflective surface, and legs (50), within the base and chamber. For more details inside chamber and base, please refer to Appendix 4 figures.

Figure 2:
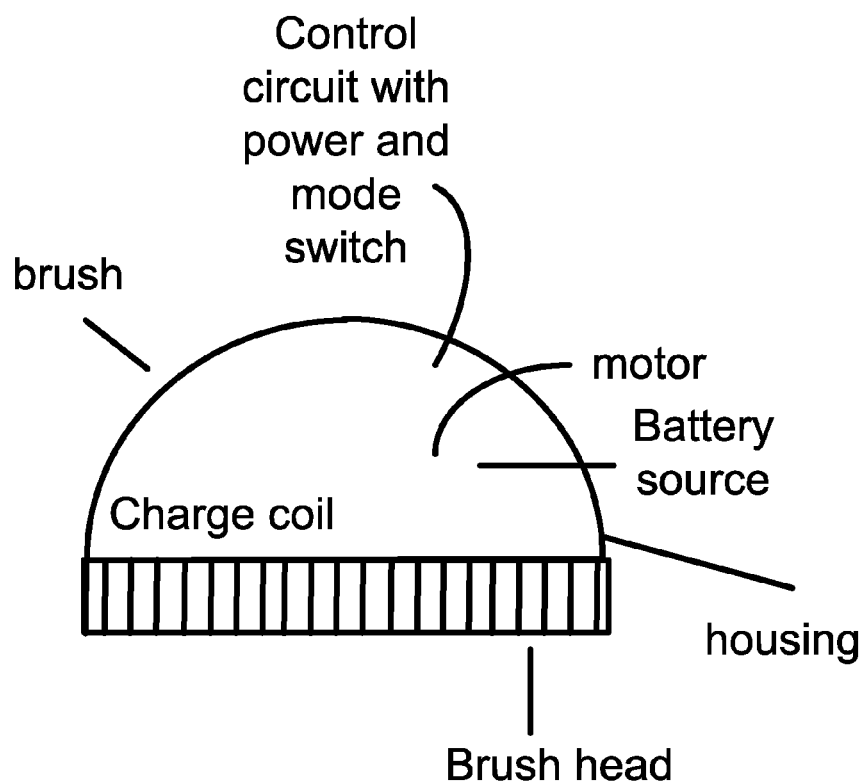
FIG. 2 is for one embodiment of our brush, as an example.

FIG. 2 is for one embodiment of our brush, as an example, with control circuit, with power and mode switch, plus motor, battery source, housing, charge coil, and brush head. For more details, please refer to Appendix 4 figures.

Figure 3:
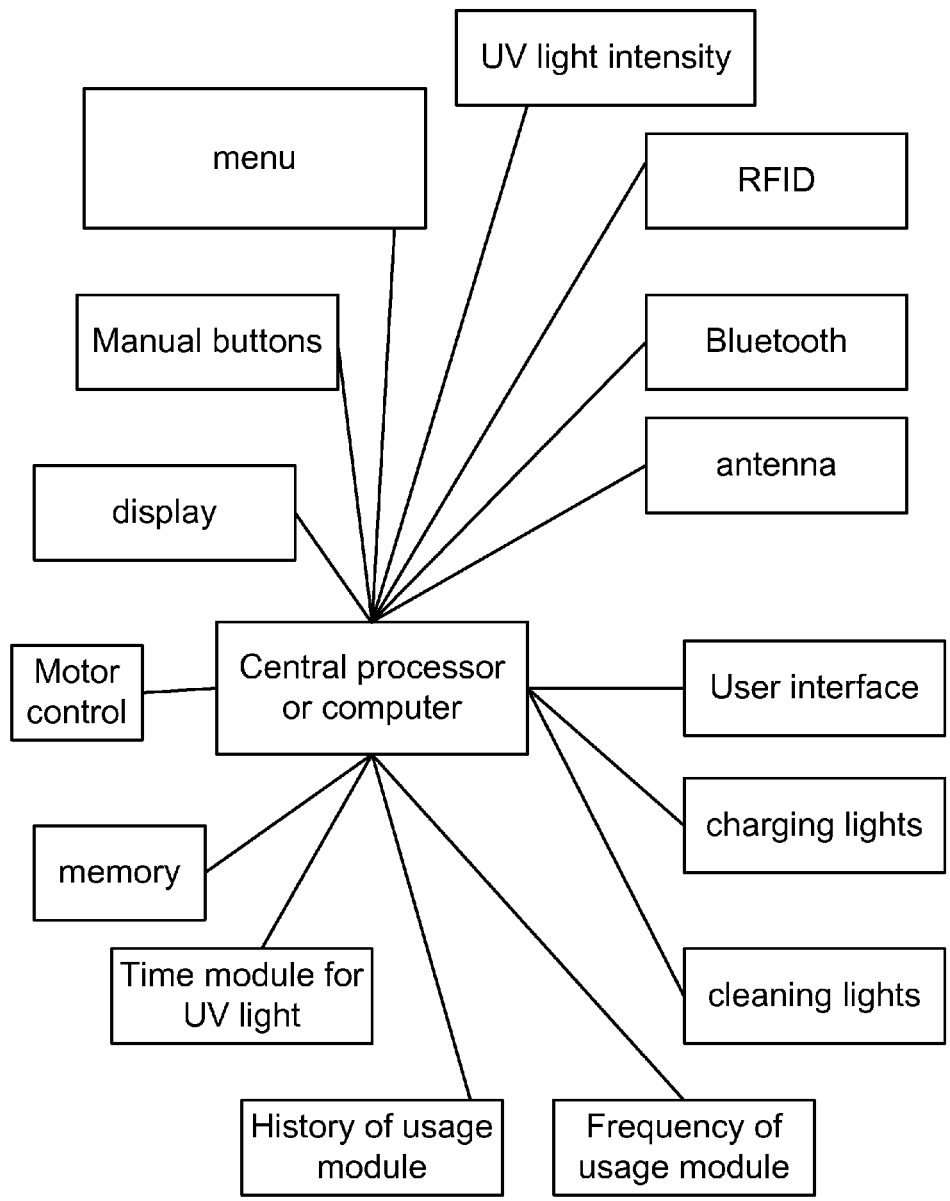
FIG. 3 is for one embodiment of our system diagram, as an example.

FIG. 3 is for one embodiment of our system diagram, as an example, with UV light set by central processor, with communication via RFID, Bluetooth, or antenna for the brush, plus menu, manual buttons, and display for the user interface, plus charging and cleaning lights indicators for the user to know. It uses history and frequency of usage for the brush, to determine time and intensity for UV light for proper cleaning, based on cleaning rules used by the processor (e.g., stored in a rules engine, for minimum intensity and time needed for the proper cleaning). The processor also controls the motor, through the motor control, for speed, direction, and ON/OFF switch.

Figure 4:
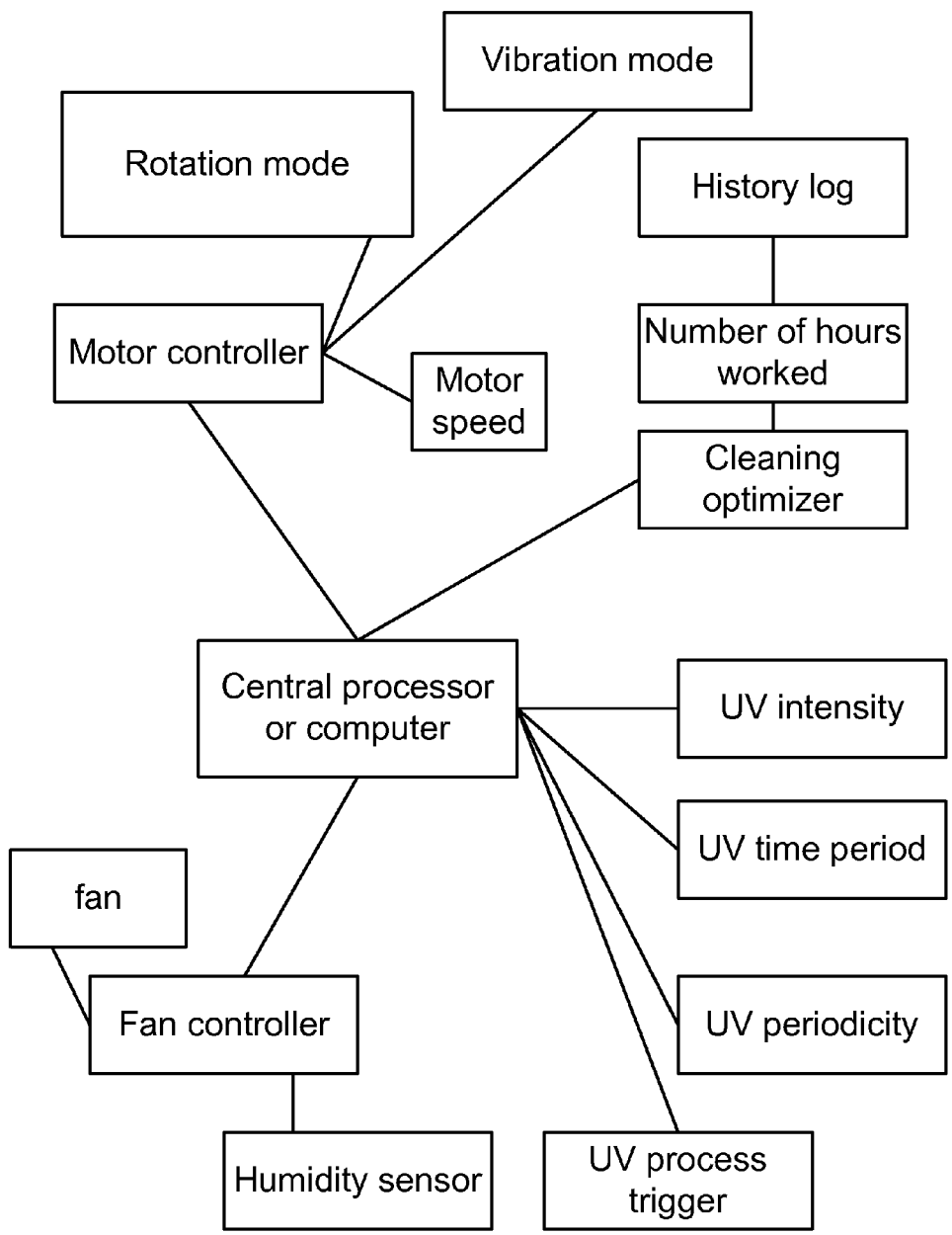
FIG. 4 is for one embodiment of our system diagram, as an example.

FIG. 4 is for one embodiment of our system diagram, as an example, with motor controller commanding the motor speed and rotation/vibration modes. The history log records the operation times for the brush, from which it calculates the total number of hours worked between the cleaning procedures, to optimize the schedule for the next cleaning, based on the rules engine, using the processor. That will set the time and intensity for UV light(s), as well as periodicity and time table for the schedule for the UV light(s). It also sets the other events that trigger the UV light. The air circulation and drying function by the fan is controlled by the fan controller, e.g., for fan speed and direction, or ramping up or down the speed. The information to start the fan comes from the humidity sensor, or other sources, e.g., showing the need to dry the brush head.

Figure 5:
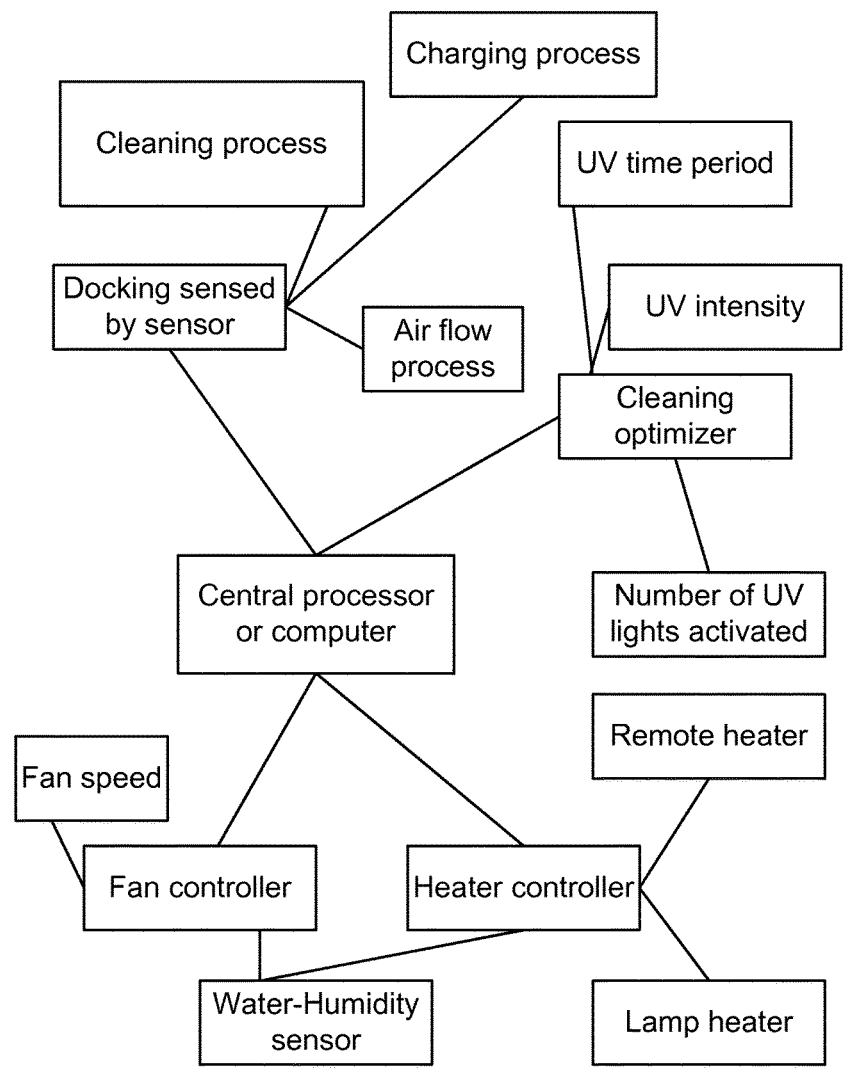
FIG. 5 is for one embodiment of our system diagram, as an example.

FIG. 5 is for one embodiment of our system diagram, as an example, with docking sensed by a sensor or switch or closing an electric circuit, e.g., using a piece of metal on the body of the brush, to indicate the full-docking on the base station. Then, it will trigger the cleaning process, charging process, or air flow process, e.g., using the fan. The cleaning optimizer sets the proper UV intensity and period for the light, with proper number of lights. The water/humidity sensor triggers fan controller for fan functions, as well as triggering heater controller, for remote heater or lamp heater functions.

Figure 6:
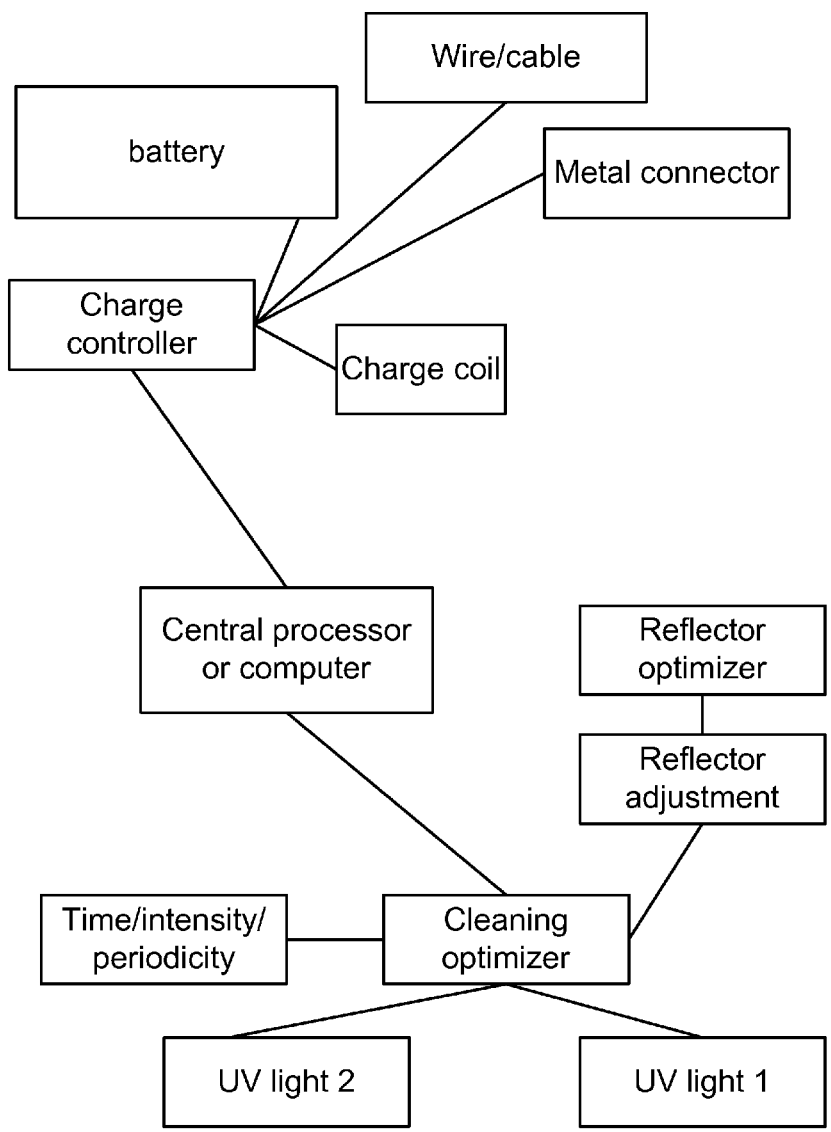
FIG. 6 is for one embodiment of our system diagram, as an example.

FIG. 6 is for one embodiment of our system diagram, as an example, with charge controller, using battery, coil, induction, cable, or metal connector. It optimizes the cleaning procedure, using multiple UV lights, with time, intensity, and periodicity specified. It also uses the optimizer to adjust the position or location of the reflectors for the system, to have the maximum UV reflection on the brush, for the best cleaning possible, with a minimum energy consumed, e.g., using convex or concave mirrors or lenses for better focusing the light on the brush head, to move or adjust the relative position, to set at the focal point or distance of the lens or mirror.

In an embodiment, we have the following system and features, from Appendix 4, for facial brush components and designs: FIG. 1 shows various facial brush landscape, with various heads and handles or bodies. FIG. 2 shows various brush motor functions, rotations, and oscillations. FIG. 3 shows orthographic projection for facial brush device, with or without brush, from different sides and views. FIG. 4 shows orthographic projection for base station with chamber, from different sides and views.

FIG. 5 of Appendix 4 shows orthographic projection for facial brush device and base station with chamber, put together, from different sides and views. FIG. 6 shows facial brush device from inside, from vertical and horizontal splits (cross sections), from different sides and views, showing: control circuit with power and mode switch, motor(s), battery source, facial brush housing, charge coil, and brush head.

Figure 7:
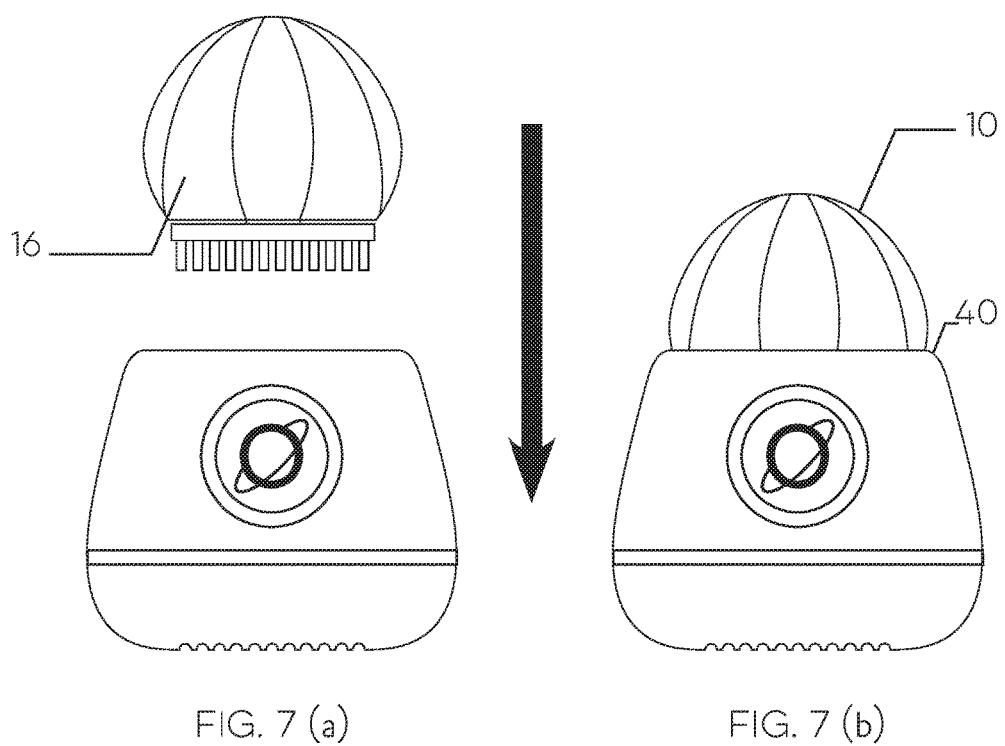
FIGS. 7a and 7b are for one embodiment of our system diagram, as an example, showing Brush Device engaging with the base, as setting in inside base, as marked between two situations shown in those 2 figures.
FIG. 7c shows a top view from inside of the chamber and base, with details of inside, for FIGS. 7a and 7b, above.
Figure 7:
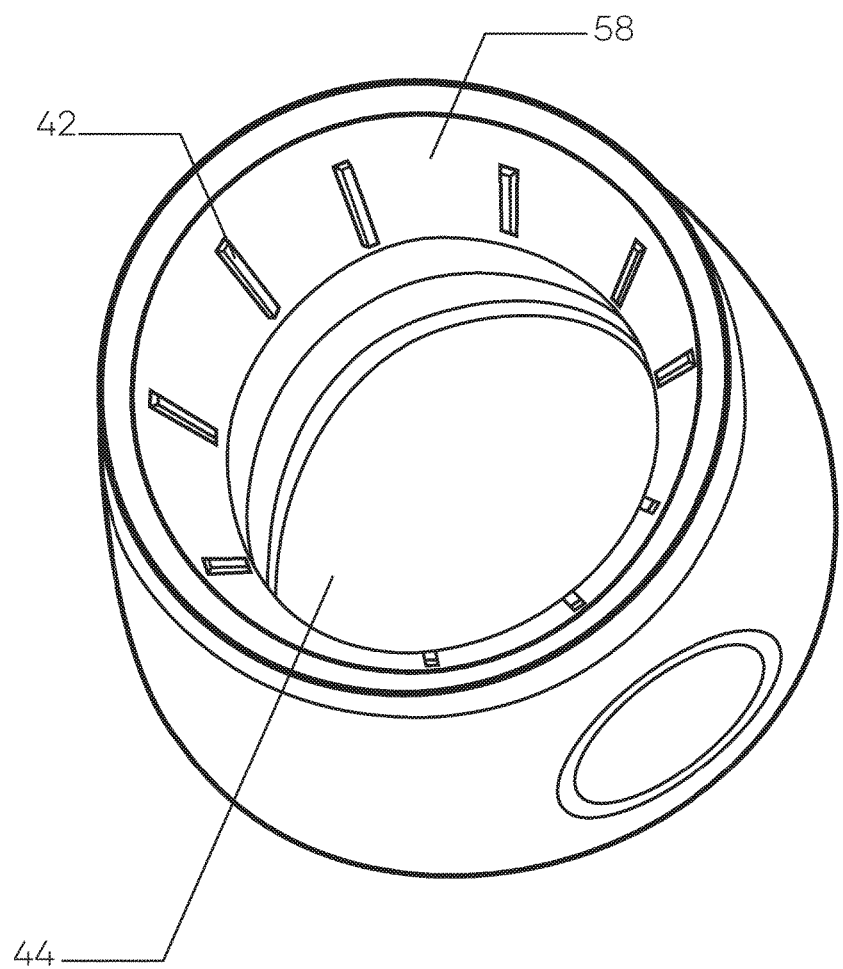

FIG. 7 of Appendix 4 shows facial brush device engaging with the base, as setting in inside base, as marked between two situations 1 and 2 in the figure. It also shows a cross sectional view from inside for charge coil, UV light source, control circuit, chamber, and the rest of the components of the device and base. It shows brush device to base station docking, with placing the Brush Device causing the activation of the UVC sequence. The chamber is a cleaning apparatus using ultraviolet rays, enhanced within a parabolic light acceleration chamber that comprises a light source and a light guide member capable of transmitting ultraviolet rays from an even light source to bathe a brush head for total immersion and maximum sterilization effect. The cleaning apparatus has a timed operation to activate the ultraviolet rays and operates as a charge station for the Brush Device.

FIG. 8 of Appendix 4 shows facial brush device engaging with the base, as setting in inside base, as marked between two situations 1 and 2 in the figure. It also shows a cross sectional view from inside for facial brush charge coil, base station charge coil, and the rest of the components of the device and base. It shows brush device to base station docking, with placing the Brush Device causing the activation of charging the circuit for the Brush Device.

Figure 9:
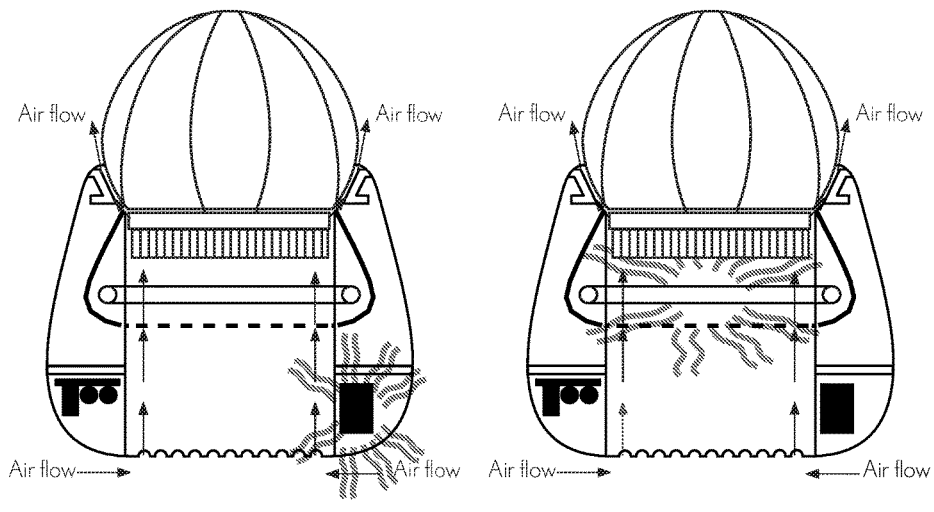
FIG. 9a is for one embodiment of our system diagram, as an example, showing that the heater increases the temperature of the air around the brush.
FIG. 9b is for one embodiment of our system diagram, as an example, showing a lamp heater.

FIG. 9 of Appendix 4 (or FIG. 8) shows Brush Device engaging with the base, as setting in inside base, with a cross sectional view from inside for reflector (62) and UV light source (46), with details of inside chamber. A parabolic light acceleration chamber comprises of an even light source to bathe a brush head (12) for total immersion and maximum sterilization effect.

Figure 10:
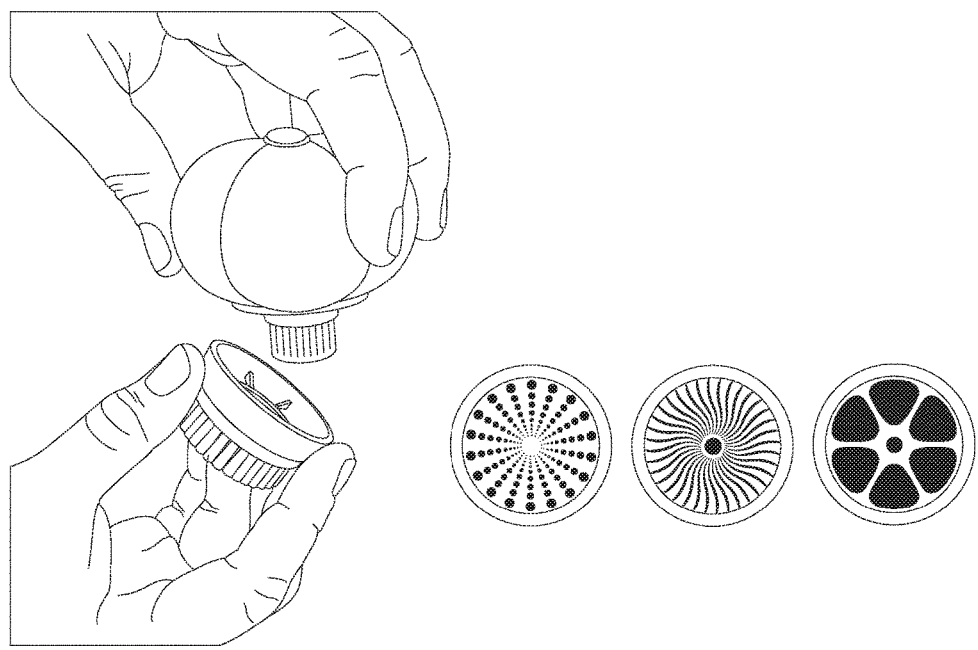
FIG. 10 is one example for the chamber cleaning brush, with multiple brush heads, exchangeable on the device.

FIG. 10 of Appendix 4 shows Brush Device engaging with the base, as setting in inside base, with a cross sectional view from inside for reflector, UV light source, control circuit, chamber, and reflective surface, with details shown. Optionally, for reflector pad, it can have further functions such as reflective surface that could further optimize the UVC light reflecting and directing up towards the brush head, as shown in the figure.

FIG. 11 of Appendix 4 shows Brush Device engaging with the base, as setting in inside base, with a cross sectional view from inside for reflector, UV light source, control circuit, chamber, and additional UVC source, with details shown. Optionally, the additional UVC source can be placed under the brush head for more coverage and wider angle of view, as shown in the figure.

FIG. 12 of Appendix 4 (or FIG. 7) shows Brush Device engaging with the base, as setting in inside base, as marked between two situations 1 and 2 in the figure (or FIGS. 7a and 7b). It also shows a top view (FIG. 7c) from inside of the chamber and base, with details of inside, along with various side views. It shows the brush to base station docking, with the small gap (80) around the brush handle and neck of the chamber is achieved through fins (42) strategically placed on the inside of the inner chamber entrance wall, as shown in the figure. This allows for brush handle to be supported on the fins, creating a gap with even distance between the handle and inner chamber wall.

FIG. 13 of Appendix 4 (or FIG. 9) shows Brush Device engaging with the base, as setting in inside base, as marked between two situations 1 and 2 in the figure. It shows function 3 (drying function). The simple sequence of facial brush placement activates the drying sequence for the facial brush head (12). It also shows the cross sections for the system with air flows and brush head, with various other components of the system, using a remote heater or a lamp heater, with the cross section of the chamber and air flow around the brush. The remote heater example (FIG. 9a) shows: 1) remote heater (52), 2) gap in base station chamber entrance (80), 3) base station chamber (40), and 4) chamber foot (64). The lamp heater example (FIG. 9b) shows: 1) lamp heater, 2) gap in base station chamber entrance (80), 3) base station chamber (40), and 4) chamber foot (64).

FIG. 14 of Appendix 4 shows Brush Device with various removable brush heads, with various shapes for various work and taste. It shows the user changing the configuration for the head. FIG. 15 of Appendix 4 shows the side views of the base station, for visual sequence of the LCD charge screen, fully illustrating the charging process.

FIG. 16 of Appendix 4 shows the side views of the Base Station, for visual sequence of the LCD cleaning screen, with self-cleaning on cycle without brush, with various cleaning intensity and time, based on the frequency of insertion and hours the device has been used recently or in total. This criteria can be used for brush cleaning, as well.

In an embodiment, we have the following system and features: A skin brush sterilization system comprising:
  A handheld skin treatment device,
  A casing containing a motor and a power source,
  A skin contacting element that is mechanically moved by the motor,
  A free-standing sterilizer,
  A housing containing a sterilization means,
  The handheld skin treatment device docks with said free-standing sterilizer,
  Said skin contacting element is exposed to said sterilization means, while a portion of said casing resides external to said housing.

In an embodiment, we have the following system and features: A skin brush sterilization system comprising:
  A handheld skin treatment device,
  A casing containing a motor and a power source,
  A skin contacting element that is mechanically moved by said motor,
  A free-standing sterilizer,
  A housing containing a sterilization means,
  The sterilization means is comprised of at least one lamp that emits light in the ultraviolet spectrum,
  At least one of the lamps is a singular light source, where the majority of its geometry can be described as a torus.

In an embodiment, we have the following system and features: A skin brush sterilization system comprising:
  A handheld skin treatment device,
  A casing containing a motor and a power source,
  A skin contacting element that is mechanically moved by said motor,
  A free-standing sterilizer,
  A housing containing a sterilization means,
  The handheld skin treatment device docks with said free-standing sterilizer,
  While docked, if debris were to fall from said skin contacting element, said debris would not contact any part of said free-standing sterilizer.

In other embodiments, we have the following system and features:
  Power source=battery or capacitor
  Skin contacting element=array of bristle tufts, foam, pumice
  Sterilization means=UV lamp or dryer
  Dryer (heater to drive moisture and/or air mover)
  Skin contacting elements are removable and replaceable
  Handheld skin treatment device has a timing means, responsive to the device being turned on, for producing successive indications of intervals of elapsed time, wherein the intervals of elapsed time are related to the desired times for treating portions of the skin, as a set of goals or targets.
  Internal parts of the sterilizer base are reflective so as to increase the coverage of the UV light.
  Portion of the skin contacting element are reflective, so as to increase the coverage of the UV light.

All the embodiments above can be combined with each other, and there is no limit on the number of combinations for mixing or adding the features mentioned above, or in this disclosure.

The following section addresses another related invention for a toothbrush system that we filed recently. Some of the teachings and features are in common with the teachings and features of our current invention here. (The previous application is titled "Toothbrush Sterilization System", Ser. No. 14/604,729, filed 25 Jan. 2015, whose teachings are also incorporated herein, by reference.)

Toothbrush Sterilization System

Toothbrushes are proven to be important for the general health and dental health of an individual. Because of the intimacy that the user shares with this particular product, the toothbrush can be a factor which promotes or extends illnesses. Because of their frequent wet nature, the portion of the brush that the user places in his/her mouth may harbor pathogens. Even a brush used exclusively by a healthy individual may have an unhealthy germ build-up over a period of time. Such germs may come from the user's own mouth and/or from the environment in which the toothbrush is kept between uses.

Most toothbrushes are kept in bathrooms, which are often fertile environments for germs. In addition to being wet, it is difficult to remove all traces of food particles from a brush after usage. These organic particles may serve as a culture for the promotion of molds and bacteria. In addition to between usage cleanliness, there is a need to ensure brushes are clean prior to their initial use. Regulations do not currently exist to require a particular level of sterilization or sanitation of toothbrushes prior to packaging and sale.

Accordingly, there is a great need for a device that effectively sanitizes toothbrushes before and between uses by consumers. And, in fact, inventions that attempt to achieve this have been known in the literature for over a century. The vast majority of these inventions involve a toothbrush and chamber. The user returns the brush to the chamber between uses. Within the chamber resides a sterilization means. Over the years, the exact nature of this sterilization means has changed—sometimes due to technology advancements, while other times due to efficacy, safety, manufacturing cost, or convenience.

TABLE 1

The table below lists several inventions that are typical of various sterilization means.

| Patent No. or SN | Issue Date or Publication Date | Inventor | Sterilization Means |
|---|---|---|---|
| 615,357 | 6 Dec. 1898 | Guilfoyle | Gas blanket |
| 757,885 | 3 Aug. 1903 | Cochkane | Liquid immersion |
| 2,579,242 | 18 Dec. 1951 | Pask | Ultraviolet lamp |
| 3,342,544 | 18 Sep. 1963 | Raymond | Aerosol or liquid spray |
| 3,884,635 | 20 May 1975 | Sloan | Dryer |
| 4,400,357 | 23 Aug. 1983 | Hoffman | Autoclave |
| 5,725,091 | 9 Mar. 1994 | Knoebel | Vacuum |

One undesirable aspect of some of the prior art is that they necessitate the bristles of the brush, or a portion of the brush in close proximity to the bristles which re-enters the user's mouth and touches on some part of the sterilization chamber, on insertion, extraction, or during the sterilization process. This undesirable contact could transfer pathogens or debris from the chamber back onto the brush and vice/versa. This causes a cross-contamination, going back-and-forth, with some residual pathogens or debris always remaining in the system. An example of this type of invention can be seen in Athon, U.S. Pat. No. 1,696,706. This invention relies on the bristles to be in frictional contact with the inside of the chamber, in order to keep the brush from falling out. Similarly, Farrar U.S. Pat. No. 2,592,131 creates a lip on which the bristles rest.

Many of the prior art inventions necessitate the user to perform additional actions to put the brush into the chamber, remove it, or activate the sterilization cycle. For example, Fowler U.S. Pat. No. 1,074,169 teaches an enclosure that fully encloses the brush. In order to insert the brush or to remove it, the user needs to open a door to gain access. This can be inconvenient if the user is already holding a container of dentifrice in one hand. Thompson U.S. Pat. No. 1,553,648 is a typical of a class of solutions where the brush can be accessed without opening a door. In these solutions the seal between the chamber and the brush assembly is accomplished by the use of a compliant stopper or a compliant chamber. The user then needs to either hold onto the chamber to keep it steady while extracting the brush or the chamber needs to be mounted to a fixed surface, e.g., a wall. Mounting is an additional action that can be inconvenient or impractical in many environments. MacShane U.S. Pat. No. 1,708,423 requires the user to perform a separate action in order to start the sterilization process.

Hecker U.S. Pat. No. 6,123,477 teaches a sterilizer that does not include a chamber. In this invention, a second brush is used to wipe down the bristles of the toothbrush. This has the obvious shortcoming that the toothbrush is exposed to the ambient environment between sterilizations instead of being protected in a chamber. In addition, the efficacy seems highly dependent on user technique. It also is only focused on sterilization of the bristles as opposed to conditioning of all the surfaces that will enter the user's mouth.

TABLE 2

The table below lists inventions that teach self-contained toothbrush sterilization and have the shortcomings described above.

| Patent No. or SN | Issue/Publ. Date | INVENTOR |
|---|---|---|
| 2,527,741 | 31 Oct. 1950 | Lamonde |
| 5,832,940 | 10 Nov. 1998 | Embry |
| 6,123,477 | 26 Sep. 2000 | Hecker |
| 6,669,390 | 30 Dec. 2003 | Porter |
| 8,168,963 | 1 May 2012 | Ratcliffe |

Lamonde, Embry, and Porter do not teach sterilization. These inventions deliver dentifrice or mouthwash. However, a sterilization fluid could be envisioned as a substitute for the dentifrice.

In all of the prior inventions that include a sterilization chamber, there is either contact between elements of the toothbrush that the user puts into his or her mouth (mentioned previously), or there exists portions of the chamber immediately below the bristles and toothbrush shaft that enter the mouth. The disadvantage with this is that fluid or particles that fall off the brush end up inside the chamber. Since the brush is put into the chamber immediately after usage, it goes in loaded with a certain amount of water. A drop of two of this water can fall off the brush, bringing along with it food particles, dentifrice, or even pathogens that have come from the user's mouth or the environment around the brush.

Some of the inventions allow for the presence of a dryer in order to drive water from the chamber (e.g. Choi U.S. Pat. No. 5,487,877). Even if the water is driven from the chamber, the particles contained within the water will remain behind. At best, this will lead to a buildup of particulates in the chamber requiring frequent cleanings. At worst, it may become a breeding ground for germs exposing the brush to a more adverse environment than if it had never entered the chamber. Many of the prior inventions rely on a completely closed chamber to ensure the sterilization means does not leak into the surrounding environment (e.g., Hurley U.S. Pat. No. 1,364,557, Eckhardt U.S. Pat. No. 6,461,568, and Barham U.S. Pat. No. 6,966,441). Thus, in summary, the prior art is very different from our invention described here in this disclosure.

For our invention, in one embodiment, we describe a method and system where the brush head and the shaft that enter the user's mouth are never contacted by the chamber. Also, below the brush head and shaft, there is no chamber. If any drops of water were to fall off the brush head, they would fall all the way through the chamber and reside on the counter on which the chamber rests. While this does not eliminate the particulate, it ensures the particulate does not reside in a chamber, which may be inaccessible or hard to clean. All particulate can be removed from the counter during regular counter cleaning routines.

In one embodiment of the present invention, our sterilization means is a UV-C lamp. This selection has advantages over the other sterilizations means. Some of them are: no spilling of fluids (vs. liquid and spray sterilization), no leakage of dangerous substances into the atmosphere (vs. gas blanket sterilization), no hot surfaces (vs. autoclave sterilization), rapid (vs. drier sterilization), and quiet (vs. vacuum sterilization). One disadvantage that UV sterilization has with respect to some of the other solutions is that it utilizes light, and light is usually associated with inherent shadows. That is, if a portion of the brush head intended for sterilization is in a shadow, the efficacy of the sterilization will be greatly reduced. Some of the prior art (e.g. Pinsky U.S. Pat. No. 7,213,603) mention multiple UV lamps as a solution to get greater coverage. This, of course, directly increases manufacturing cost and would require a significant number of bulbs in order to achieve uniform coverage. Other prior art address this shortcoming by introducing reflective surfaces on the inside of the chamber. This also increases manufacturing costs. A typical method to create surfaces such as this is to sputter metal onto molded plastic surfaces. While effective, composite parts like this are difficult to recycle.

In the present invention, we show a single lamp, but that lamp is in a ring configuration (otherwise known as annular, torus, or donut), which is unique from the prior art. The brush end of the toothbrush is placed within the ring so that light approaches the brush head from a greater number of angles, and shadows are much reduced or eliminated. In practice, because of the end conditions of the lamp, the ring is interrupted. However, this interruption is minor (small distance) and most of the lamp retains the toroidal shape and the advantages thereof (with good coverage of the toothbrush, from all angles). Here, we provide more details for the toothbrush system/device:

The attached invention describes an electronic toothbrush sterilization system that is used by consumers. This invention introduces many new features that allow for improved cleanliness, convenience, and robustness. Toothbrush sterilization systems are known in the industry and have been available for quite some time. Originally, the toothbrushes were manual, just comprised of a handle and bristles. The sterilization source has changed over the years.

Originally, the brushes were immersed in a sterilization fluid to kill germs present on the brush. Prior art of this technique was seen as early as 1904. Later (~1918), gases (e.g. formaldehyde) were used. There has also been evidence of heat-based sterilization methods and aerosol usage. Later (~1940s), because of convenience and effectiveness, the sterilization source was changed to that of a light, which bathes the toothbrush in light in the UVC range. This light has a spectral wavelength centered roughly around 240 nm. The wavelength range of UVC light is 100-280 nm. While the light sources may emit light outside of this range (into the visible spectrum, for example), it is the light within this range that has germicidal benefits.

In the 1950s the first electronic toothbrushes were introduced. These were initially targeted toward users with reduced motor skills. Later, it became apparent that many of these devices had a greater effectiveness compared to manual brushes, when it came to cleaning teeth. The earliest brushes were plugged into an AC outlet. However, in the 1960s, battery powered versions were introduced and started being adopted widely.

Electronic toothbrushes can be categorized into two groups depending on the motion the bristles are driven. One group employs vibration. The majority of these vibration toothbrushes today are called ultrasonic toothbrushes, since the vibration of the bristles is above 20 kHz (which is the upper limit of human hearing).

The second major category of electronic toothbrushes is rotational. With these, the bristles rotate continuously or oscillate in a rotating manner about an axis.

Products that sterilize electronic toothbrushes have been known for some time as well. In these systems, there is a charging circuit that keeps the batteries in the toothbrush handle fully charged. In addition, there is a UVC light source that shines on the bristles. In all the currently shipping products that we are aware of, the brush head is detached from the handle for the sterilization process. The bristles, along with a short section of shaft (which is defined collectively in this document as the brush head), are placed into a separate chamber that contains the UVC light source, and the light is activated.

The disadvantages of the current state-of-the-art electronic toothbrush sterilization systems are described below:

(1) When the user has finished brushing his/her teeth, the handle is returned to the charging station. This is very convenient as the station reserves some countertop real estate for the product, and the user knows precisely where the product is when they need to use it again. However, to actually sterilize the bristles, extra effort is needed to separate the brush head from the handle and place it in the sterilization chamber. While this is not a lot of extra work, it turns out that many users choose not to sterilize the brush head after each brushing. This creates the opportunity for pathogens (e.g. virus, bacteria, parasite, or fungus) to grow on the wet head of the brush, which is a terrible result.

(2) When the brush head is removed from the handle and placed in the sterilization container, the toothbrush is not immediately ready for use. The handle is present, but there is no brush head attached to it. The brush head needs to be removed from the sterilization container and reattached to the handle.

(3) When the brush head remains attached to the handle after use and is not placed in the sterilization chamber, it is exposed to the environment. This environment is typically a bathroom environment that has many sources of water flow (e.g. sinks, showers, toilets and bathtubs). These water sources aerosolize water droplets. These water droplets can transport other elements such as urine, feces, and saliva throughout the bathroom. Since the bristles are exposed to this environment, they can become inadvertently contaminated.

(4) In the existing devices, the sterilization chamber has a closed bottom with one opening where the brush head is inserted and removed. In addition, this chamber often has many acute internal angles within and between various parts (i.e., nooks and crannies). Bristles that are placed in this environment are wet (having just been used). This water can and does drip off the bristles and stays behind in the chamber. These pools of water, if not in direct line of sight to the UVC light source can fester and grow a community of pathogens.

(5) The light source in the existing sterilization chamber is either a point light source or a line light source. This invariably creates shadows in the bristle area, where the light is not as effective as it is not bathing the entirety of the bristles.

(6) The existing systems go though the same cleaning cycle regardless of the number of times the brush has been used between cleanings.

(7) The sterilization chamber is very difficult to clean.

(8) The light source in the existing systems is very accessible to the user. In fact, the user can inadvertently touch the light source with his/her hand or with the brush head. This could add contaminants (e.g., oil or particulate matter) to the surface of the light, thereby reducing its emission and efficacy.

One embodiment of the current invention incorporates an integrated charging station and sterilization chamber. This base station is either corded to AC power or runs on its own internal batteries. The electronic toothbrush is inserted into the base station with the brush head end down. Once it is inserted, the brush head is removed from the environment, which keeps it cleaner and more sterile than being left in the environment between brushings. This helps to solve the issue raised in the current art, mentioned in the section above.

The toothbrush has an internal charging coil near the brush head end. This creates a non-contact inductive coupling between this coil and a similar coil in the base. Once the base detects the presence of the toothbrush, the charging commences and the sterilization cycle begins. The sterilization is accomplished by means of a UVC light source within the charging station. This UVC light source could be a point or a line source similar to the current state of the art. In one embodiment, it is a light source that wraps around the brush head eliminating shadows mentioned in the section above.

This ring light could be a mercury vapor tube light. It could also be a series of point light sources that wrap around the brush head. Alternatively, there could be a single light source that is brought up to and surrounds the brush head via a light pipe. To further aide in the elimination of shadows, the interior of the sterilization chamber could be made reflective. Aluminum coatings have been shown to reflect UVC light very effectively. During the sterilization cycle, the UVC light turns on for a pre-determined amount of time. The amount of time could vary based on the number of brush cycles that the toothbrush has been through since the last cleaning. This addresses problem in Section above.

The brush handle can keep track of usage and this information can be communicated to the base station via means such as RFID tracking or Bluetooth communication. Once the brush is inserted in the base, the sterilization cycle commences. Since this takes no additional effort to accomplish from the user, it addresses the shortcomings of the current products referenced in Sections above.

The chamber of the preferred design is devoid of crevices that could become water traps. If water drips off the brush head, the water falls through the device through an opening in the bottom of the chamber. This addresses the current problem stated in Section above. This water could reside on the countertop until it evaporates away.

Alternatively, there could be a hydrophilic pad that resides below the chamber. This pad could wick the water throughout its volume or along its surface. Because the water is spread out, it has more evaporative surface area and is lost to the environment at a significantly accelerated rate. This pad could have other functions in that it could cradle and prevent the unit from tipping over. Because the chamber is open on both ends and is lacking in crevices, it is easy to clean with a device such as a baby bottle cleaner, an attachment to the toothbrush or even a towel addressing the concern of Section above.

Since there can be a communication link between the brush and the base station, either of those could have a display to communicate information to the user. This display can show things like charging time remaining, sterilization time remaining, number of brushing cycles completed, life of brush head remaining, and average brushing duration, among others.

When the brush is being inserted into the base station, the design is such that the bristles are prevented from touching the light source. The light source is also buried deep within the chamber, which minimizes the possibly of the user touching it directly. This goes to addressing problem of Section (8) mentioned above.

All the foregoing could be applied to a manual as well as electrical toothbrush.

Appendix 1 includes the following: FIG. 9 shows the UV bulb and shadowed area in the chamber or casing. FIG. 10 shows the chamber from different views. FIG. 11 shows brush to chamber docking, the placement, and the gap. FIG. 12 shows RFID chip and the cross section of the brush. FIG. 13 shows the UV light source and inside the chamber. FIG. 14 shows inside the chamber with the reflective surface, like mirror, for maximum effect. FIG. 15 shows the UV bulb, with curvature, circle shaped. FIG. 16 shows the chamber pad, its shape, and its usage, as well as indicator light and/or display options on the chamber's outside surface, for warning or information for the user, e.g., for charged left on the device, and amount of brushing time or frequency, e.g., with multiple lights or diodes, or bar shaped light or indicator, or sliding scale indicator, or colored lights, or light of varying intensity proportional to the value of the indicated parameter, e.g., light intensity proportional to the charge left on the battery, or using red light as warning for low charge indication. FIG. 17 shows chamber cleaning brush. FIG. 20 shows brush to chamber activation. FIG. 22 shows cleaning cycle sequence, for self-cleaning. FIG. 23 shows charging cycle sequence. FIG. 24 shows the description and advantages of our chamber/toothbrush system and their designs/parameters/components. FIG. 25 shows cleaning procedure (Function 1). FIG. 26 shows charging procedure (Function 2). FIG. 27 shows advanced sonic brush, with components, from different angles. FIG. 28 shows the inside chamber with details. FIG. 29 shows the inside chamber with UV light source ring. FIG. 30 shows the brush placement, in motion. FIG. 31 shows the light pipe inside chamber. FIG. 32 shows the retractable cable or wire for our system, for compact and clean setup, with optional spring to retract the wire, e.g., located at the inside bottom of the chamber, with optional hook to release the spring for retraction process. FIG. 33 shows drying procedure/sequence (Function 3), with gaps for drying process, with thermal energy or radiant energy, as options, with convection, conduction, or radiation mechanism, with increased airflow, with some air coming from the gaps around the chamber's legs or feet. The units or devices for thermal energy or radiant energy can be inserted into the middle of the chamber cavity, as moveable parts, or they can be stationary, on the walls or in the middle of the chamber.

Appendix 2, pages 1-11, show different views of the chamber and toothbrush with more details and cross-sectional views.

In one embodiment, we have multiple chambers on the unit for (to hold) multiple toothbrushes, e.g., with common power supply or battery backup for the toothbrushes and UV light sources. In one embodiment, we have multiple rings for the UV light sources in the same chamber. In one embodiment, the multiple rings for the UV light sources are in parallel to each other. In one embodiment, we have multiple rings for the UV light sources parallel to the ground or countertop. In one embodiment, we have multiple rings for the UV light sources at an angle to the horizontal ground or countertop, e.g., at 15, 30, 40, 45, 55, 60, or 80 degrees, with respect to the horizontal ground.

In one embodiment, we have some fins or tracks or grooves on the inside body of chamber and/or on the toothbrush handle (or both) to cause some gaps between the toothbrush and inside chamber for air to flow, for better drying process and better drainage of the water, when the toothbrush is set in the chamber after each use (See, e.g., FIG. 11, Appendix 1).

In one embodiment, we have batteries and charging coil inside the toothbrush body, with RFID chip mounted on or inside the system, for communication with a computer, smart phone, and chamber, e.g., for transmission of the data, authentication, and identification, e.g., for display of the time of usage, remaining charge of the device, and the like, for both versions of RFID (active & passive). (See, e.g., FIG. 12, Appendix 1) In one embodiment, we have Bluetooth devices for short range communications, one being installed on toothbrush and/or chamber.

In one embodiment, the source of the UV is inside the chamber. In one embodiment, the source of the UV is outside the chamber, e.g., coming from the fiber optics or waveguides to the chamber. In one embodiment, the light gets split to multiple rays by a splitter on its way, for a better coverage of the object to be cleaned. (See, e.g., FIG. 31, Appendix 1) In one embodiment, there is a mirror or sets of mirror or reflection surface or curved reflective surface inside the chamber, focusing the light or directing the light on the toothbrush for cleaning, e.g. spherical or cylindrical or conical shape, as concave mirror or surface, e.g., using metal coating. (See, e.g., FIG. 13, Appendix 1)

In one embodiment, the focus area is on focal point of the mirror. In one embodiment, the source can be a ring or thick ring or multiple rings or parallel rings or horizontal rings or array of rings or rings with various wavelengths in UV range (or diodes or lasers or other light sources). (See, e.g., FIG. 14, Appendix 1)

In one embodiment, the chamber cleaning brush, with multiple brush heads, exchangeable on the device (FIG. 10) or on the toothbrush body or on a separate rod or stick, is used to clean the chamber by the user. (See, e.g., FIG. 17, Appendix 1) It can have multiple brushes on the same stick or bar or rod, with different shapes, for better cleaning.

In one embodiment, the chamber light, menu, or display can give choices to the user for functionalities, e.g., inputting data by user, or give information or warning to user, e.g., using color lights or diodes, to indicate the charging stages for the toothbrush, or malfunction of a component, using a warning red light. (See, e.g., FIG. 20, Appendix 1)

FIG. 21, Appendix 1 shows cleaning cycle sequence. Note that the selective cleaning intensity is based on the frequency of the brush insertion, e.g.: The higher the frequency, the higher the intensity. This intensity (I) can be linear proportional (with k as coefficient) or non-linear proportional to the frequency value (f), for different embodiments. For example, one case may be: (I=k*f), where I is the intensity of the light, and f is the frequency or number of brushing or length of time of brushing per unit time, e.g., per week or month or day (or average value, or running-average, or cumulative average), wherein * denotes the multiplication operation. The intensity can be based on: Radiant intensity, measured in watts per steradian (W/sr), or Luminous intensity, measured in lumens per steradian (lm/sr), or candela (cd), or Irradiance or Intensity, measured in Watts per meter squared (W/m2), or Radiance, measured in (W·sr-1·m-2).

In one embodiment, the charging is done by direct metal contact and wiring, with backup battery or rechargeable battery. In one embodiment, the charging is done by inductive coil, remotely, with no direct or metal contact. The material of the chamber can be any synthetic or natural material, as in the prior art, e.g., plastic. In one embodiment, the brush and contour of the inside chamber are designed such that they do not touch or cross-contaminate. (See, e.g., FIG. 30, Appendix 1)

FIGS. 1-11 of Appendix 3 correspond to various features and figures of Appendix 2. FIG. 5 is for one embodiment of our device, as an example, for a view of the chamber. FIGS. 1-4, 8-10 are for embodiments of our device, as examples, for views of the chamber with a toothbrush. FIG. 6 (or FIG. 7) is for one embodiment of our device, as an example, for a view of the chamber with a toothbrush in it, as a cross section. FIG. 11 is for one embodiment of our device, as an example, for a view of the toothbrush.

Appendix 5 is for one embodiment of our system, as an example, for a view of the components of our system, comprising: menu, manual buttons, and display; RFID, Bluetooth, and antenna; user-interface, indicator lights, and warning lights; frequency of usage, history of usage, averaging module (to average values for comparisons, for baseline values, or for history or performance values, so far), and memory; motor control; UV lamp; brush dryer; mode lights; charging circuit; and external power supply.

Other embodiments are, with their variations and examples:
A dental hygiene system, comprising of:
An oral care implement with a handle at one end, a mouth care end effect at the distal end, and a shaft between the two.
The mouth care end effect and said shaft enter the user's mouth during normal usage.
A free-standing chamber for storing said oral care implement.
Said chamber contains a sterilization means.
While stored or during sterilization, if debris were to fall from said mouth care end effect or said shaft, said debris would not contact any part of said chamber.
Said mouth care end effect resides below said handle, while stored.
A heater to drive moisture from the said end effect.
The oral care implement is electronic and battery powered.
Said chamber includes a charging circuit to charge the batteries of said oral care implement.
A dental hygiene system, comprising of:
An oral care implement with a handle at one end, a mouth care end effect at the distal end, and a shaft between the two.
Said mouth care end effect and said shaft enter the user's mouth during normal usage.
A free-standing chamber for storing said oral care implement, where said mouth care end effect and said shaft reside inside the chamber, while at least a portion of said handle resides outside.
Said chamber contains a sterilization means.
Said chamber does not contact said mouth care end effect, nor said shaft, when inserting, removing, or storing within said chamber.
Said oral care implement can be inserted or removed from said chamber without additional actions taken upon said chamber or said oral care implement.
Said chamber is open to the environment (gravitationally) below said mouth care end effect and said shaft, during sterilization and storage.
Said mouth care end effect resides below said handle, while stored.
A heater to drive moisture from the said end effect.
The oral care implement is electronic and battery powered.
Said chamber includes a charging circuit to charge the batteries of said oral care implement.
A dental hygiene system, comprising of:
An oral care implement.
A free-standing chamber for storing said oral care implement.
Said chamber contains a sterilization means.
Said sterilization means is comprised of at least one lamp that emits light in the ultraviolet spectrum.
At least one of said lamps is a singular light source, where the majority of its geometry can be described as a torus.
Any variations of the above teaching are also intended to be covered by this patent application. Any 2 or more embodiments can also be combined and added together, from examples above, both from toothbrush and/or facial brush.

The invention claimed is:

1. A facial or body cleaning brush system, said system comprising:
   a base station;
   a brush device;
   wherein said brush device comprises a brush head;
   wherein said brush device sits on top of said base station;
   wherein said base station has a cavity, directly opening to floor or ground at bottom for air passage, stretching from top to bottom of said base station, and inclusive of top and bottom of said base station;
   wherein of said base station, only said cavity resides directly below said brush head, when said brush device sits on top of said base station;
   at least a leg, groove, fin, or gap, on or under said base station, to let air in.

2. The facial or body cleaning brush system as recited in claim 1, said system comprises a fan.

3. The facial or body cleaning brush system as recited in claim 1, said system comprises a cleaning optimizer and a cleaning scheduler.

4. The facial or body cleaning brush system as recited in claim 1, said system comprises one or more ultraviolet lights.

5. The facial or body cleaning brush system as recited in claim 1, said system comprises one or more motors.

6. The facial or body cleaning brush system as recited in claim 1, said system comprises one or more reflectors.

7. The facial or body cleaning brush system as recited in claim 1, said system comprises a humidity sensor.

8. The facial or body cleaning brush system as recited in claim 1, said system comprises a motor controller.

9. The facial or body cleaning brush system as recited in claim 1, said system comprises a motor, with rotational and oscillating motor action options.

10. The facial or body cleaning brush system as recited in claim 1, said system comprises changeable brush tips or brush heads.

11. The facial or body cleaning brush system as recited in claim 1, said system comprises a charge coil module.

12. The facial or body cleaning brush system as recited in claim 1, said system comprises a battery.

13. The facial or body cleaning brush system as recited in claim 1, said system comprises a concave or convex lens, mirror, or reflector.

14. The facial or body cleaning brush system as recited in claim 1, said system comprises a remote heater or a lamp heater.

15. The facial or body cleaning brush system as recited in claim 1, said system comprises a charge indicator display.

16. The facial or body cleaning brush system as recited in claim 1, said system comprises a cleaning indicator display.

17. A facial or body cleaning brush system, said system comprising:
    a base station;
    said base station comprises a chamber;
    wherein said chamber is a cavity, stretching from top to bottom of said base station, and inclusive of top and bottom of said base station;
    a brush device;
    wherein said brush device comprises a brush head;
    a light source that emits ultraviolet light;
    wherein said light source is circular in shape, covering all circumference of cross section of said chamber;
    a humidity sensor;
    a microprocessor;
    a fan;
    said humidity sensor is connected to said microprocessor;
    said microprocessor controls a fan controller;
    said microprocessor controls a heater controller;
    said fan controller controls said fan's speed;
    said microprocessor controls said light source;
    said microprocessor controls said light source's process trigger;
    said microprocessor controls a cleaning optimizer;
    said cleaning optimizer controls a cleaning scheduler;
    said microprocessor controls said light source's periodicity, time period, and intensity.

18. A facial or body cleaning brush system, said system comprising:
    a base station;
    said base station comprises a chamber;
    wherein said chamber is a cavity, stretching from top to bottom of said base station, and inclusive of top and bottom of said base station;
    a brush device;
    wherein said brush device comprises a brush head;
    a fan;
    wherein said fan moves air inside said cavity;
    said brush head is exchangeable;
    a chamber cleaning brush;
    said chamber cleaning brush is clipped on said brush device.

* * * * *